(12) United States Patent
Van Dam et al.

(10) Patent No.: US 9,282,968 B2
(45) Date of Patent: Mar. 15, 2016

(54) APPLICATOR FOR ENDOSCOPIC TREATMENT OF BILIARY DISEASE

(75) Inventors: Jacques Van Dam, San Carlos, CA (US); J. Craig Milroy, Palo Alto, CA (US); R. Matthew Ohline, Redwood City, CA (US)

(73) Assignee: TREUS MEDICAL, INC., Redwood City, CA (US)

( * ) Notice: Subject to any disclaimer, the term of this patent is extended or adjusted under 35 U.S.C. 154(b) by 96 days.

(21) Appl. No.: 12/951,803

(22) Filed: Nov. 22, 2010

(65) Prior Publication Data
US 2011/0071350 A1   Mar. 24, 2011

Related U.S. Application Data

(63) Continuation of application No. 12/277,443, filed on Nov. 25, 2008, now abandoned.

(60) Provisional application No. 60/991,682, filed on Nov. 30, 2007, provisional application No. 61/033,368, filed on Mar. 3, 2008.

(51) Int. Cl.
*A61B 17/11*   (2006.01)
*A61F 2/04*   (2013.01)
*A61M 27/00*   (2006.01)
(Continued)

(52) U.S. Cl.
CPC .............. *A61B 17/1114* (2013.01); *A61B 17/11* (2013.01); *A61F 2/04* (2013.01); *A61M 27/008* (2013.01); *A61B 2017/00278* (2013.01); *A61B 2017/1139* (2013.01); *A61F 2/064* (2013.01); *A61F 2/24* (2013.01); *A61F 2/2493* (2013.01); *A61F 2002/041* (2013.01); *A61M 25/1002* (2013.01); *A61M 29/02* (2013.01);
(Continued)

(58) Field of Classification Search
CPC .............. A61B 17/11; A61B 17/1114; A61B 2017/00278; A61B 2017/1139; A61F 2/04; A61F 2002/041; A61F 2/064; A61M 27/008; A61M 2025/0233; A61M 2025/1072; A61M 25/1002; A61M 29/02
USPC ...................................... 604/8, 540, 264, 275
See application file for complete search history.

(56) References Cited

U.S. PATENT DOCUMENTS 2,127,903 A   8/1938   Bowen
3,818,511 A   6/1974   Goldberg et al.
(Continued)

FOREIGN PATENT DOCUMENTS

EP   0 779 062       6/1997
EP   1 044 663 A2   10/2000
(Continued)

OTHER PUBLICATIONS

Final Office Action received for U.S. Appl. No. 13/410,281 dated May 10, 2013.
(Continued)

*Primary Examiner* — Kami A Bosworth
*Assistant Examiner* — Brandy S Lee
(74) *Attorney, Agent, or Firm* — Foley & Lardner LLP

(57) ABSTRACT

A device for treating biliary disease includes a component configured for deployment to a lumen of a gallbladder or gallbladder duct. The component has a proximal end and a distal end with a lumen extending therethrough and a fluid or gas delivery apparatus at its distal end.

19 Claims, 7 Drawing Sheets

(51) Int. Cl.

| | | |
|---|---|---|
| A61B 17/00 | (2006.01) | |
| A61F 2/06 | (2013.01) | |
| A61F 2/24 | (2006.01) | |
| A61M 25/10 | (2013.01) | |
| A61M 29/02 | (2006.01) | |
| A61M 25/02 | (2006.01) | |

(52) U.S. Cl.
CPC ............... *A61M2025/0233* (2013.01); *A61M 2025/1072* (2013.01)

(56) References Cited

U.S. PATENT DOCUMENTS

| | | | |
|---|---|---|---|
| 3,834,394 A | | 9/1974 | Hunter et al. |
| 3,933,040 A | | 1/1976 | Thompson |
| 4,085,757 A | | 4/1978 | Pevsner |
| 4,263,917 A | | 4/1981 | Moss |
| 4,352,358 A | | 10/1982 | Angelchik |
| 4,699,611 A | | 10/1987 | Bowden |
| 4,781,677 A | | 11/1988 | Wilcox |
| 4,900,303 A | | 2/1990 | Lemelson |
| 4,955,859 A | | 9/1990 | Zilber |
| 4,966,294 A | | 10/1990 | Mack et al. |
| 4,968,294 A | | 11/1990 | Salama |
| 4,994,066 A | | 2/1991 | Voss |
| 5,071,419 A | | 12/1991 | Rydell et al. |
| 5,159,925 A | | 11/1992 | Neuwirth et al. |
| 5,167,614 A | | 12/1992 | Tessmann et al. |
| 5,170,805 A | | 12/1992 | Kensey et al. |
| 5,171,311 A | | 12/1992 | Rydell et al. |
| 5,197,948 A | | 3/1993 | Ghodsian |
| 5,201,746 A | | 4/1993 | Shichman |
| 5,259,847 A | | 11/1993 | Trambert |
| 5,270,805 A | | 12/1993 | Abe et al. |
| 5,334,210 A | | 8/1994 | Gianturco |
| 5,364,400 A | | 11/1994 | Rego et al. |
| 5,443,449 A | | 8/1995 | Buelna |
| 5,454,788 A | | 10/1995 | Walker et al. |
| 5,466,242 A | | 11/1995 | Mori |
| 5,499,994 A | | 3/1996 | Tihon et al. |
| 5,514,088 A | | 5/1996 | Zakko |
| 5,536,248 A | | 7/1996 | Weaver et al. |
| 5,632,762 A | | 5/1997 | Myler |
| 5,643,254 A | | 7/1997 | Scheldrup et al. |
| 5,709,224 A | | 1/1998 | Behl et al. |
| 5,741,333 A | | 4/1998 | Frid |
| 5,743,905 A | | 4/1998 | Eder et al. |
| 5,755,769 A | | 5/1998 | Richard et al. |
| 5,776,126 A | | 7/1998 | Wilk et al. |
| 5,800,341 A | * | 9/1998 | McKenna et al. ............. 600/109 |
| 5,817,046 A | | 10/1998 | Glickman |
| 5,824,071 A | | 10/1998 | Nelson et al. |
| 5,853,419 A | | 12/1998 | Imran |
| 5,860,426 A | | 1/1999 | Kleiman |
| 5,876,432 A | | 3/1999 | Lau et al. |
| 6,019,757 A | | 2/2000 | Scheldrup |
| 6,077,261 A | | 6/2000 | Behl et al. |
| 6,165,210 A | | 12/2000 | Lau et al. |
| 6,241,762 B1 | | 6/2001 | Shanley |
| 6,245,101 B1 | | 6/2001 | Drasler et al. |
| 6,246,914 B1 | | 6/2001 | De La Rama et al. |
| 6,283,992 B1 | | 9/2001 | Hankh et al. |
| 6,312,404 B1 | * | 11/2001 | Agro et al. ................. 604/95.02 |
| 6,358,247 B1 | * | 3/2002 | Altman et al. .................. 606/41 |
| 6,406,491 B1 | | 6/2002 | Vanney |
| 6,409,755 B1 | | 6/2002 | Vrba |
| 6,416,545 B1 | | 7/2002 | Mikus et al. |
| 6,468,303 B1 | | 10/2002 | Amplatz et al. |
| 6,544,291 B2 | | 4/2003 | Taylor |
| 6,558,429 B2 | | 5/2003 | Taylor |
| 6,585,754 B2 | | 7/2003 | Wallace et al. |
| 6,599,299 B2 | | 7/2003 | Schultz |
| 6,610,100 B2 | | 8/2003 | Phelps et al. |
| 6,616,675 B1 | | 9/2003 | Evard et al. |
| 6,641,610 B2 | | 11/2003 | Wolf et al. |
| 6,655,386 B1 | | 12/2003 | Makower et al. |
| 6,663,663 B2 | | 12/2003 | Kim et al. |
| 6,746,489 B2 | | 6/2004 | Dua et al. |
| 6,764,519 B2 | | 7/2004 | Whitmore, III |
| 6,945,949 B2 | | 9/2005 | Wilk |
| 6,949,080 B2 | | 9/2005 | Wolf et al. |
| 6,962,602 B2 | | 11/2005 | Vardi et al. |
| 6,964,681 B2 | | 11/2005 | Murray, III |
| 7,004,949 B2 | | 2/2006 | Yencho et al. |
| 7,011,095 B2 | | 3/2006 | Wolf et al. |
| 7,041,110 B2 | | 5/2006 | Yencho et al. |
| 7,094,260 B2 | | 8/2006 | Jing et al. |
| 7,118,600 B2 | | 10/2006 | Dua et al. |
| 7,144,363 B2 | | 12/2006 | Pai et al. |
| 7,182,744 B2 | | 2/2007 | Yamasaki et al. |
| 7,294,115 B1 | | 11/2007 | Wilk |
| 2001/0044647 A1 | | 11/2001 | Pinchuk et al. |
| 2002/0032487 A1 | | 3/2002 | Dua et al. |
| 2002/0055768 A1 | | 5/2002 | Hess et al. |
| 2002/0095110 A1 | | 7/2002 | Vanney et al. |
| 2002/0156523 A1 | | 10/2002 | Lau et al. |
| 2003/0045828 A1 | | 3/2003 | Wilk |
| 2003/0055484 A1 | | 3/2003 | Lau et al. |
| 2003/0069533 A1 | * | 4/2003 | Kakutani et al. .................. 604/8 |
| 2003/0069606 A1 | | 4/2003 | Girouard et al. |
| 2003/0083734 A1 | | 5/2003 | Friedrich et al. |
| 2003/0149472 A1 | | 8/2003 | Pinchuk et al. |
| 2003/0163079 A1 | | 8/2003 | Burnett |
| 2003/0216733 A1 | * | 11/2003 | McClurken et al. ............ 606/51 |
| 2004/0073317 A1 | | 4/2004 | Schultz |
| 2004/0093058 A1 | | 5/2004 | Cottone et al. |
| 2004/0102855 A1 | | 5/2004 | Shank |
| 2004/0181150 A1 | | 9/2004 | Evans et al. |
| 2004/0199262 A1 | | 10/2004 | Dua et al. |
| 2004/0211434 A1 | | 10/2004 | Loomas et al. |
| 2004/0215331 A1 | | 10/2004 | Chew et al. |
| 2004/0249335 A1 | | 12/2004 | Faul et al. |
| 2004/0249470 A1 | | 12/2004 | Whitmore, III |
| 2005/0010275 A1 | | 1/2005 | Sahatjian et al. |
| 2005/0010280 A1 | | 1/2005 | Jing et al. |
| 2005/0021084 A1 | | 1/2005 | Lu et al. |
| 2005/0107733 A1 | | 5/2005 | Faul et al. |
| 2005/0137707 A1 | | 6/2005 | Malek |
| 2005/0149166 A1 | | 7/2005 | Schaeffer et al. |
| 2005/0159726 A1 | | 7/2005 | Evans et al. |
| 2005/0171598 A1 | | 8/2005 | Schaeffer |
| 2005/0192659 A1 | | 9/2005 | Dahl et al. |
| 2005/0216074 A1 | | 9/2005 | Sahatjian et al. |
| 2005/0228413 A1 | | 10/2005 | Binmoeller et al. |
| 2005/0273060 A1 | | 12/2005 | Levy et al. |
| 2005/0277964 A1 | | 12/2005 | Brenneman et al. |
| 2005/0277965 A1 | | 12/2005 | Brenneman et al. |
| 2006/0047337 A1 | | 3/2006 | Brenneman |
| 2006/0058864 A1 | | 3/2006 | Schaeffer et al. |
| 2006/0106455 A1 | | 5/2006 | Furst et al. |
| 2006/0129221 A1 | | 6/2006 | Heruth |
| 2006/0135963 A1 | | 6/2006 | Kick et al. |
| 2006/0155369 A1 | | 7/2006 | Edwin et al. |
| 2006/0235269 A1 | * | 10/2006 | Waxman ....................... 600/104 |
| 2006/0247575 A1 | | 11/2006 | Cartledge et al. |
| 2007/0016306 A1 | | 1/2007 | Dua et al. |
| 2007/0021828 A1 | | 1/2007 | Krolik et al. |
| 2007/0038283 A1 | | 2/2007 | Mustapha |
| 2007/0043381 A1 | | 2/2007 | Furst et al. |
| 2007/0043391 A1 | | 2/2007 | Moszner et al. |
| 2007/0055358 A1 | | 3/2007 | Krolik et al. |
| 2007/0067011 A1 | | 3/2007 | Krolik et al. |
| 2007/0073376 A1 | | 3/2007 | Krolik et al. |
| 2007/0073388 A1 | | 3/2007 | Krolik et al. |
| 2007/0088425 A1 | | 4/2007 | Schaeffer |
| 2007/0173867 A1 | | 7/2007 | Brenneman |
| 2007/0173921 A1 | | 7/2007 | Wholey et al. |
| 2007/0179592 A1 | | 8/2007 | Schaeffer |
| 2007/0225634 A1 | * | 9/2007 | Ferren et al. .................... 604/27 |
| 2007/0249985 A1 | | 10/2007 | Brenneman et al. |
| 2007/0293940 A1 | | 12/2007 | Schaeffer et al. |
| 2008/0195171 A1 | | 8/2008 | Sharma |
| 2008/0243151 A1 | | 10/2008 | Binmoeller et al. |
| 2009/0143713 A1 | | 6/2009 | Van Dam et al. |

(56) References Cited

U.S. PATENT DOCUMENTS

| | | | |
|---|---|---|---|
| 2009/0143759 A1 | 6/2009 | Van Dam et al. | |
| 2009/0143760 A1 | 6/2009 | Van Dam et al. | |
| 2009/0306633 A1* | 12/2009 | Trovato et al. | 604/891.1 |
| 2011/0054381 A1 | 3/2011 | Van Dam et al. | |
| 2011/0071350 A1 | 3/2011 | Van Dam et al. | |
| 2011/0071566 A1 | 3/2011 | Dam et al. | |

FOREIGN PATENT DOCUMENTS

| | | |
|---|---|---|
| EP | 1 044 663 A3 | 3/2001 |
| EP | 1 314 404 A2 | 5/2003 |
| EP | 1 314 404 A3 | 9/2003 |
| EP | 1 795 151 A1 | 6/2007 |
| GB | 2 460 287 | 11/2009 |
| JP | 03-009746 A | 1/1991 |
| JP | 11-076412 | 3/1999 |
| JP | 15-116982 | 4/2003 |
| RU | 2226364 | 4/2004 |
| SU | 620262 | 8/1978 |
| SU | 688185 | 9/1979 |
| SU | 1131498 | 12/1984 |
| SU | 1586687 | 8/1990 |
| SU | 1634257 | 3/1991 |
| SU | 1828745 | 7/1993 |
| WO | WO-96/13296 A1 | 5/1996 |
| WO | WO-97/27898 A1 | 8/1997 |
| WO | WO-00/12832 A2 | 3/2000 |
| WO | WO-00/18325 A1 | 4/2000 |
| WO | WO-00/12832 A3 | 6/2000 |
| WO | WO-01/58384 A1 | 8/2001 |
| WO | WO-2004/069097 A2 | 8/2004 |
| WO | WO-2006/062996 A2 | 6/2006 |
| WO | WO-2006/127784 A2 | 11/2006 |
| WO | WO-2007/005010 A1 | 1/2007 |
| WO | WO-2007/014283 A2 | 2/2007 |
| WO | WO-2006/127784 A3 | 5/2007 |
| WO | WO-2007/050628 A2 | 5/2007 |
| WO | WO-2007/050628 A3 | 1/2008 |
| WO | WO-2006/062996 A3 | 4/2009 |
| WO | WO-2007/014283 A3 | 4/2009 |
| WO | WO-2009/073507 A2 | 6/2009 |
| WO | WO-2009/073507 A3 | 6/2009 |
| WO | WO-2009/073515 A2 | 6/2009 |
| WO | WO-2009/073515 A3 | 6/2009 |
| WO | WO-2009/073521 A2 | 6/2009 |
| WO | WO-2009/073521 A3 | 5/2012 |
| WO | WO-2012/071031 A1 | 5/2012 |

OTHER PUBLICATIONS

British Search Report received for British Appln. No. 0821930.5 dated Mar. 19, 2009.
European Search Report received for EP 08856414.1 completed Feb. 22, 2012.
Final Office Action received for U.S. Appl. No. 12/277,443 dated Jun. 21, 2010.
International Search Report and Written Opinion received for PCT/US2008/084830 dated Jun. 24, 2009.
International Search Report and Written Opinion received for PCT/US2008/084865 dated Jun. 24, 2009.
International Search Report and Written Opinion received for PCT/US2008/084888 dated Jul. 17, 2009.
Non-final Office Action received for U.S. Appl. No. 12/277,443 dated Oct. 22, 2009.
Non-final Office Action received for U.S. Appl. No. 12/959,264 dated Sep. 12, 2011.
Non-final Office Action received for U.S. Appl. No. 13/410,281 dated Jan. 17, 2013.
Non-Final Office Action in U.S. Appl. No. 13/410,281 dtd Oct. 28, 2013 (11 pages).
Final Office Action in U.S. Appl. No. 13/410,281 dtd Mar. 10, 2014 (11 pages).
Non-final Office Action received for U.S. Appl. No. 13/410,281 dated Sep. 12, 2014.
US Office Action on U.S. Appl. No. 13/439,251 Dtd Nov. 12, 2014.
US Office Action on U.S. Appl. No. 13/410,281 Dtd Feb. 24, 2015.
US Office Action on U.S. Appl. No. 13/410,281 Dtd Jul. 2, 2015.
US Office Action on U.S. Appl. No. 13/439,251 Dtd May 27, 2015.

* cited by examiner

APPLICATOR FOR ENDOSCOPIC TREATMENT OF BILIARY DISEASE

CROSS-REFERENCE TO RELATED APPLICATIONS

This application is a continuation application that claims priority under 35 U.S.C. §120 to U.S. patent application Ser. No. 12/277,443, which claims the benefit of U.S. Provisional Application No. 60/991,682, filed Nov. 30, 2007, and U.S. patent application Ser. No. 61/033,368, filed Mar. 3, 2008, which are incorporated herein by reference.

This application has related subject matter to U.S. Utility patent application Ser. No. 12/277,338, filed Nov. 25, 2008, entitled "Methods, Devices, Kits and Systems for Defunctionalizing the Cystic Duct" by Jacques Van Dam, J. Craig Milroy, and R. Matthew Ohline and U.S. Utility patent application Ser. No. 12/277,491, filed Nov. 25, 2008, entitled, "Biliary Shunts, Delivery Systems, Methods of Using the Same, and Kits Therefor" by Jacques Van Dam, J. Craig Milroy, and R. Matthew Ohline, which applications are incorporated herein by reference.

FIELD OF THE INVENTION

The invention described in this patent application addresses challenges confronted in the treatment of biliary disease. Biliary disease includes conditions affecting the gallbladder, cystic duct, and common bile duct.

Biliary System Function and Anatomy:

Bile is a greenish-brown digestive fluid produced by the liver 10 illustrated in FIG. 1, and is vital for the digestion of fatty foods. Bile is secreted by liver cells and collected by a network of ducts that converge at the common hepatic duct 12. While a small quantity of bile drains directly into the lumen of the duodenum 30 (the section of small intestine immediately downstream of the stomach), most travels through the common hepatic duct 12 and accumulates in the lumen of the gallbladder 14. Healthy gallbladders are pear-shaped sacs with a muscular wall that, on average, measure 10 cm in length and can store approximately 50 ml of fluid within its lumen. When fatty foods are ingested, the hormone cholecystokinin is released, which causes the gallbladder 14 to contract. Contraction of the gallbladder 14 forces bile to flow from the gallbladder 14, through the cystic duct 16, into the common bile duct 18, out the papilla 28, and finally into the duodenum 30 of the small intestine. Here, it mixes and reacts with the food that exits the stomach. The Sphincter of Oddi 26 controls secretions from the liver, pancreas 24, and gallbladder 14 into the duodenum 30 of the small intestine. The opening on the inside of the descending duodenum 30 after the Sphincter of Oddi 26 is called the major duodenal papilla 28 (of Vater). Together, the biliary ducts, the gallbladder 14, the cystic duct 16 and the common bile duct 18 comprise the biliary system (FIG. 1).

The pancreas 24 is a gland organ in the digestive and endocrine system of vertebrates. It is both an endocrine gland (producing several important hormones, including insulin, glucagon, and somatostatin), as well as an exocrine gland, secreting pancreatic juice containing digestive enzymes that pass to the small intestine. These enzymes help in the further breakdown of the carbohydrates, protein, and fat in the chyme. The pancreatic duct 22, or duct of Wirsung, is a duct joining the pancreas 24 to the common bile duct 18 to supply pancreatic juices which aid in digestion provided by the exocrine pancreas. The pancreatic duct 22 joins the common bile duct 18 just prior to the major duodenal papilla 28, after which both ducts perforate the medial side of the second portion of the duodenum 30 at the major duodenal papilla.

Biliary Disease:

The most common problem that arises in the biliary system is the formation of gallstones, a condition called cholelithiasis. Approximately 20 million Americans have gallstones, and about 1-3% will exhibit symptoms in any given year. In the US, gallstones are more common among women, with 25% of women having gallstones by the age of 60 and 50% by the age of 75. Pregnancy and hormone replacement therapy increase the risk of forming gallstones. Prevalence is lower for American men: approximately 25% will develop gallstones by the age of 75. In the US, gallstones are responsible for the highest number of hospital admissions due to severe abdominal pain.

Gallstones 20, 20' are most often composed of cholesterol, but may also be formed from calcium bilirubinate, in which case they are called pigment stones. They range in size from a few millimeters to several centimeters, and are irregularly shaped solids resembling pebbles. They can form in the gallbladder 14, cystic duct 16, and/or the common bile duct 18 (FIG. 2). By themselves, gallstones 20 do not necessarily result in disease states. This is the case 90% of the time. However, stones can cause infection and inflammation, a condition known as cholecystitis, which is generally the result of restricting or blocking the flow of bile from the gallbladder 14 and common bile duct 18, or the fluids secreted by the pancreas 24.

Gallbladder disease may be chronic, and patients who suffer from this may periodically experience biliary colic. Symptoms include pain in the upper right abdomen near the ribcage, nausea, and/or vomiting. The pain may resolve within an hour of onset, may prove unresponsive to over-the-counter medicines, and may not decrease with changes of position or the passage of gas. Recurrence is common, with pain often recurring at the same time of day, but with frequency of less than once per week. Fatty or large meals may cause recurrence several hours after eating, often awakening the patient at night. Patients may elect to suffer from these symptoms for very long periods of time, such as years or even decades.

Patients with chronic cholecystitis have gallstones and low-grade inflammation. Untreated, the gallbladder 14 may become scarred and stiff over time, leading to a condition called dysfunctional gallbladder. Patients who have chronic cholecystitis or dysfunctional gallbladder may experience gas, nausea, and abdominal discomfort after meals, and chronic diarrhea.

Acute cholecystitis (a surgical emergency) develops in 1-3% of those with symptomatic gallstone disease, and is due to obstruction of the common bile duct 18 or cystic duct 16 by stones or sludge. Symptoms are similar to biliary colic, though they are more severe and persistent. Pain in the upper right abdomen can be constant and severe, the intensity may increase when drawing breath, and it may last for days. Pain may radiate to the back, under the breastbone or the shoulder blades, and it may be perceived on the left side of the abdomen. In addition to nausea and vomiting, one third of patients experience fever and chills. Complications from acute cholecystitis can be serious and life threatening, and include gangrene, abscesses, perforation of the gallbladder 14 which can lead to bile peritonitis, pus in the gallbladder wall (empyema), fistulae, and gallstone ilius (when a gallstone creates a blockage in the small intestine).

When gallstones 20' become lodged in the common bile duct 18 (FIG. 2), the condition is known as choledocholithiasis. Symptoms for this condition include pain, nausea and vomiting, and some patients develop jaundice, have dark urine and/or lighter stools, rapid heartbeat, and experience an abrupt drop in blood pressure. These symptoms can also be accompanied by fever, chills, and/or severe pain in the upper right abdomen. Complications from choledocholithiasis can also be very serious, and include infection of the common bile duct 18 (cholangitis) and inflammation of the pancreas 24 (pancreatitis).

A smaller patient population suffers from gallbladder disease that occurs in the absence of gallstones. This condition, called acalculous gallbladder disease, can also be chronic or acute. Chronic acalculous gallbladder disease, also called biliary dyskinesia, is thought to be caused by motility disorders that affect the gallbladder's ability to store and release bile. Acute acalculous gallbladder disease occurs in patients who suffer from other serious illnesses which can lead to inflammation of the gallbladder 14 because of a reduction in the supply of blood to the gallbladder 14 or a reduced ability to contract and empty bile into the duodenum 30.

Cancer can also develop in the gallbladder 14, though this condition is rare. Gallstones have been found in 80% of patients with gallbladder cancer. Gallbladder cancer typically develops from polyps, which are growths inside the gallbladder 14. When polyps 15 mm across or larger are observed, the gallbladder is removed as a preventive measure. Polyps smaller than 10 mm are widely accepted as posing low risk and are not generally removed. When detected early, before the cancer has spread beyond the mucosa (inner lining) of the gallbladder, the 5-year survival rate is approximately 68%. However, gallbladder cancer is not usually detected until patients are symptomatic, by which time the disease is more advanced.

Treatment of Biliary Disease:

The most effective treatment for biliary disease has been surgical removal of the gallbladder 14, a procedure called cholecystectomy. Surgical removal of the gallbladder 14 is indicated for patients who experience a number of less severe gallstone attacks, cholecystitis, choledocholithiasis, pancreatitis, acalculous biliary pain with evidence of impaired gallbladder 14 emptying, those at high risk for developing gallbladder cancer, and those who have previously undergone endoscopic sphincterotomy for common bile duct stones. Other treatment modalities exist and are frequently used, but gallbladder disease tends to recur in the majority of patients who forgo cholecystectomy and pursue alternatives. Removal of the gallbladder 14 is highly successful at permanently eliminating biliary disease. Cholecystectomy is one of the most commonly performed procedures on women. The gallbladder 14 is not an essential organ, and after a period of adjustment post surgery, patients tend to return to more or less normal digestive function.

Cholecystectomy can be performed either as open surgery, which requires a single larger incision in the upper right abdomen, or laparoscopic surgery, in which several small instruments are inserted through much smaller incisions in the abdomen. Approximately 80% of cholecystectomies are performed laparoscopically. The primary benefits of this minimally invasive approach are faster recovery for the patient, and a reduction in overall healthcare costs. Patients who receive laparoscopic cholecystectomy are usually released the same day. By contrast, patients receiving open cholecystectomies typically spend 5-7 days in a hospital before release. 5-10% of laparoscopic procedures convert to open procedures when difficulties arise, such as injury to major blood vessels, inadequate access, inadequate visualization, previous endoscopic sphincterotomy, and thickened gallbladder wall. Complications from cholecystectomy (open or laparoscopic) include bile duct injuries (0.1-0.5% for open, 0.3-2% with a declining trend for laparoscopic), pain, fatigue, nausea, vomiting, and infection. In up to 6% of cases, surgeons fail to identify and remove all gallstones present.

In some cases, the degree of infection and inflammation prevents patients from undergoing immediate cholecystectomy. In these cases, the gallbladder 14 must be treated with antibiotics and anti-inflammatory agents, and drained through a tube into a reservoir outside the abdomen. Placement of this tube occurs in a procedure called percutaneous cholecystostomy, in which a needle is introduced to the gallbladder 14 through the abdomen, fluid is withdrawn, and a drainage catheter is inserted. This catheter drains into an external bag which must be emptied several times a day until the tube is removed. The drainage catheter may be left in place for up to 8 weeks. In cases where no drainage catheter is inserted, the procedure is called gallbladder aspiration. Since no indwelling catheter is placed, the complication rate for gallbladder aspiration is lower than that of percutaneous cholecystostomy.

Treatment methodologies other than cholecystectomy include expectant management, dissolution therapy, endoscopic retrograde cholangiopancreatography (ERCP) with endoscopic sphincterotomy, and extracorporeal shockwave lithotripsy (ESWL).

Expectant management is appropriate for patients who have gallstones but no symptoms, and for non-emergency cases with less severe symptoms. This approach is not recommended when patients are in high risk categories (e.g. high risk for gallbladder cancer) or have very large gallstones (e.g. greater than 3 cm).

Oral dissolution therapy involves the administration of pills containing bile acids that can dissolve gallstones. This approach is only moderately effective, and the rate of recurrence of gallstones after completion of treatment is high. It is not appropriate for patients with acute inflammation or stones in the common bile duct (more serious conditions). Dissolution therapy tends to be more effective for patients with cholesterol stones, and is sometimes used in conjunction with lithotripsy. Despite its relative ineffectiveness, it is costly: treatment can last up to 2 years and the drugs cost thousands of dollars per year.

Related to oral dissolution therapy is contact dissolution, a procedure that involves injection of a solvent such as methyl tert-butyl ether (MTBE) directly into the gallbladder 14. This approach is highly effective at dissolving gallstones, but patients may experience severe burning pain.

ERCP (endoscopic retrograde cholangiopancreatography) is a procedure in which an endoscope is introduced through the mouth of a patient, past the stomach to the papilla 28, where the common bile duct 18 empties into the duodenum 30. The overall goal of the procedure is to insert instruments and tools into the common bile duct 18 via the papilla 28 in order to treat biliary disease. Typically, endoscopic sphincterotomy is performed, which is a procedure that enlarges the opening of the papilla 28 in the small intestine. This can be accomplished surgically or via balloon dilation. Contrast agent is introduced into the common bile duct 18 to visualize the biliary tree fluoroscopically. Tools for clearing blockages, such as mechanical lithotripsy devices, can be deployed to crush gallstones and remove the resulting debris. Drainage catheters and stents may also be inserted to facilitate the drainage of bile past obstructions. Complications from this challenging procedure occur at a rate of 5-8%, and include recurrence of stone formation, pancreatitis, infection, bleeding, and perforation.

Extracorporeal shockwave lithotripsy (ESWL) is a technique in which focused, high-energy ultrasound is directed at the gallbladder 14. The ultrasound waves travel through the soft body tissue and break up the gallstones. The resulting stone fragments are then usually small enough to pass through the bile duct into the small intestine. Oral dissolution therapy is often used in conjunction with ESWL. This treatment is not in common use, as less than 15% of the patient population are good candidates. However, ESWL is used to treat patients who are not candidates for surgery. Complications from ESWL include pain in the gallbladder area, pancreatitis, and failure of the gallstone fragments to pass into the small intestine.

SUMMARY OF THE INVENTION

An aspect of the invention is directed to devices for treating biliary disease. Suitable devices comprise: a component configured for defunctionalizing a gallbladder of a patient which has a proximal end and a distal end with a lumen extending therethrough and one or more apertures at a distal end adaptable to deliver a fluid to a lumen within the gallbladder or a gallbladder duct. Other suitable devices comprise: a means for defunctionalizing a gallbladder of a patient having a proximal end and a distal end with a lumen extending therethrough and one or more means for accessing the lumen at a distal end adaptable to deliver a fluid to a lumen within the gallbladder or a gallbladder duct. The distal end of the device can be configured to provide an angular orientation, to deliver a fluid with at least one of a 360 degree radial pattern, a sharp stream, and a cone shape, and/or to have an articulating member. Additionally, the device can further be adapted to apply a vacuum. The devices can further provide a means for applying a vacuum. In some instances, the lumen includes a means for restricting fluid flow. In some instances, the distal end is adapted to apply an adhesive to a lumen of the gallbladder. Devices can also be configured for deployment by an endoscope, a needle, guidewire, or guidance catheter. In some instances, the lumen is configurable to provide restrictable fluid flow, such as with the use of one or more fluid control components. Alternatively, one or more valves can be used, including at least one of a flow-restrictor or one-way valve. Additionally, devices can be configured such that they are flexible. In some configurations, the device is an elongate tube adapted and configured to extend into the gastrointestinal tract.

An aspect of the invention is directed to a method of treating biliary disease. The method comprises the steps of: accessing a lumen associated with a gallbladder or a gallbladder duct; defunctionalizing at least one of the gallbladder duct or the gallbladder; and leaving the gallbladder in situ. Additionally, the step of defunctionalizing the gallbladder can further comprise the step of delivering a substance to at least one of the gallbladder duct or the gallbladder, for example, such that it occupies a lumen of at least one of the gallbladder duct or the gallbladder, and/or is one or more of antibiotics, inflammatory agents, and anti-inflammatory agents. Delivery of substances can be performed sequentially or concurrently, as desired. Another aspect of the method includes the step of preventing bile from entering the gallbladder lumen. In some aspects the method further comprises the step of localizing the gallbladder via endoscopic ultrasound. In other aspects of the invention, the method can comprise the step of accessing the gallbladder via the gastrointestinal tract, such as via a duodenum. In still other aspects of the methods the step of defunctionalizing at least one of the gallbladder duct or the gallbladder further comprises one or more of sclerosing, necrotizing or ablating tissue. Suitable ablation techniques include, for example, cryoablation, thermal ablation, chemical ablation, radio frequency ablation, microwave ablation, and ultrasound ablation. Fluid delivery can be achieved with an angular orientation, or with at least one of a 360 degree radial pattern, a sharp stream, and a cone shape. Moreover, the step of delivering a fluid can be achieved with a device comprising an articulating member. Defunctionalizing at least one of the cystic duct or the gallbladder can further comprise applying a vacuum to a lumen of the cystic duct or the gallbladder, applying an adhesive to the lumen of the gallbladder duct or the gallbladder, and/or physically blocking a lumen of the gallbladder duct or the gallbladder. In some instances, the additional steps of altering gallstones and/or removing gallstones can also be performed. Similarly, obstructions can be cleared within the gallbladder. In other aspects of the invention, the method includes the step of visualizing a treatment area. Additionally, the device can be delivered via an endoscope, via a needle, via a guidewire or via a guidance catheter. The method can also include the step of restricting flow from the gallbladder lumen to the gastrointestinal tract, such as by operating a valve to restrict fluid flow. Additionally, the step of defunctionalizing the gallbladder can be performed in situ. The step of defunctionalizing can be achieved by delivering a substance into a space within the gallbladder, such as by delivering a gel or foam. In some instances the delivered substance, such as the gel or foam, can be activated in situ. Moreover, the amount of substance delivered can fill, or substantially fill, the gallbladder lumen either upon delivery or activation. Defunctionalizing can also be achieved by one or more of sclerosing or necrotizing a tissue within the gallbladder, such as by using an ablation technique such as cryoablation, thermal ablation, chemical ablation, radio frequency ablation, ultrasound ablation, and microwave ablation.

Yet another aspect of the invention is directed to kits for treating biliary disease. Kits can comprise: (a) a device adaptable to deliver to a lumen of a gallbladder or gallbladder duct; and optionally (b) a compound for delivery to a tissue. Additional components of a kit can include, for example, one or more of: a catheter, a needle, a guidewire, and a guidance catheter. Additionally, the kits can include an ablation device. One or more agents can also be included in the kit including, for example, a sclerosing agent, antibiotics, inflammatory agents, anti-inflammatory agents, biocompatible gels, and biocompatible foams. Still other components of the kits can include, for example, one or more of a pair of scissors, a scalpel, a swab, a syringe, a hemostat, a lubricant, a needle, a snare, an antiseptic, and an anesthetic.

Another aspect of the invention is directed to the use of any of the devices disclosed herein for use in the treatment of biliary disease.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention will be set forth with particularity in any claims presented based on this application. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Devices, systems, methods and kits provided herewith can obviate the need for a plurality of procedures, including, for example: 1) percutaneous cholecystostomy, 2) cholecystectomy, 3) percutaneous trans-hepatic cholangiography (PTHC), and 4) endoscopic retrograde cholangiopancreatography (ERCP). Additionally, disclosed treatment modalities enable treatment of a distal common bile duct 18 obstruction, e.g. secondary to pancreatic carcinoma, cholangiocarcinoma, and/or ampullary carcinoma. As will be appreciated by those skilled in the art, the conventional standard of care for treating biliary disease has been surgical removal of the gallbladder 14 and closure of the cystic duct 16. While this has proven to be an effective mechanism for permanently eliminating biliary disease and its recurrence, the present invention seeks to accomplish the same end in a less invasive and less costly way. This may be achieved by treating biliary disease without requiring the removal of the gallbladder 14. Methods and apparatus are described in this application that are intended to effectively treat biliary disease with the gallbladder 14 and cystic duct 16 left in situ by defunctionalizing the gallbladder.

Defunctionalization of the Gallbladder:

By treating the gallbladder in situ in such a way that the biliary disease necessitating treatment is addressed and the likelihood of recurrence is low or altogether eliminated, the need for additional treatment, e.g. cholecystectomy, may be obviated. One method for achieving these goals may be defunctionalization of the gallbladder. A gallbladder that is treated and remains in situ but is otherwise non-functional may lead to the desired result. Alternatively, for example, this goal may be achieved by altering the configuration of the gallbladder 14 in such a way that the underlying condition is addressed and prevented from recurring. The gallbladder can be accessed by any suitable mechanism including, percutaneously, endoscopically, laparoscopically, and the like. Moreover, any of the materials and substances delivered to the gallbladder can be delivered concurrently or sequentially. Delivery of substances can occur sequentially in time or the sequence of delivery can be separated by seconds, minutes, or hours.

Figure 3:
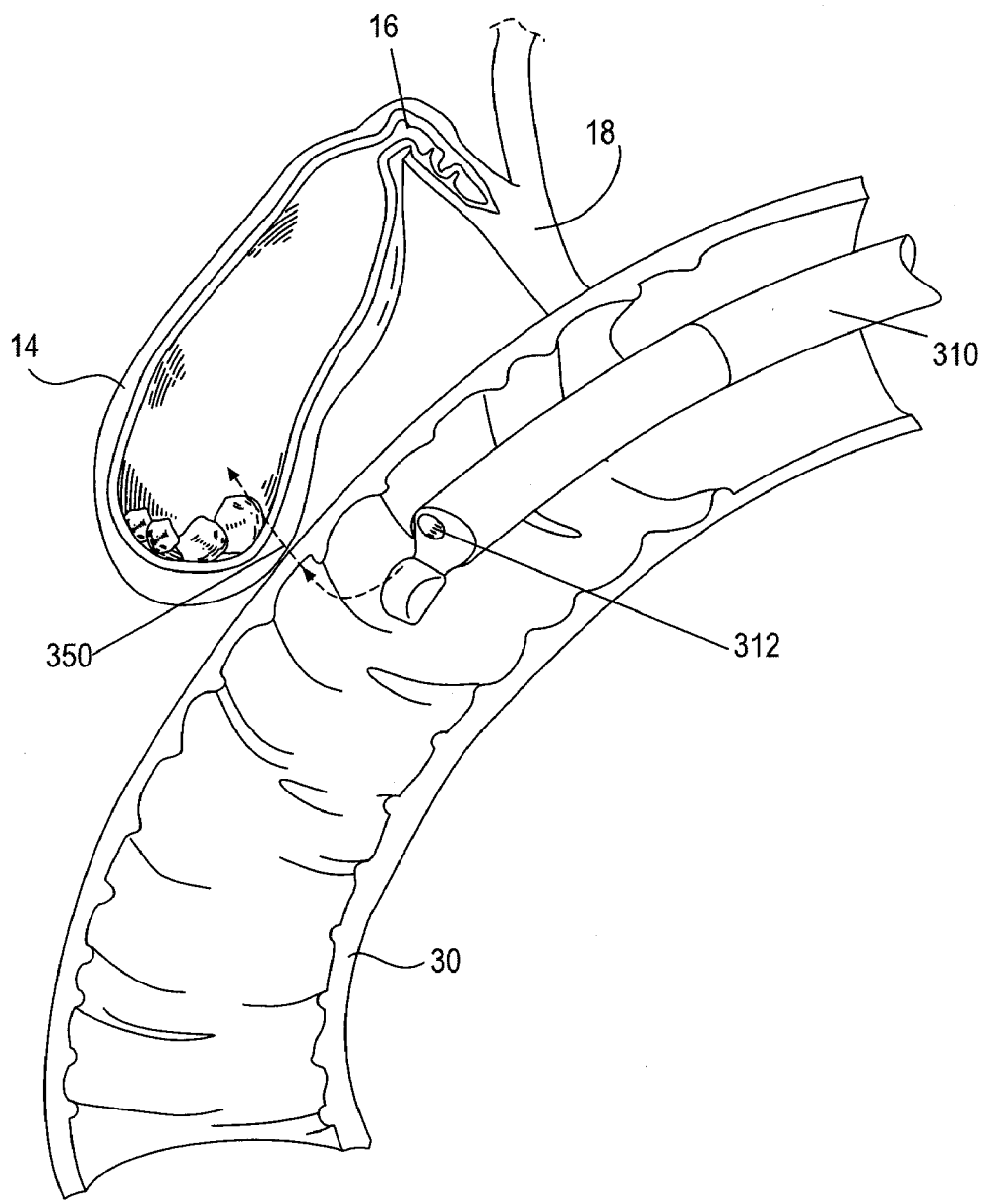
FIG. 3 illustrates an endoscope accessing the biliary system via the intestinal system.

A method of treating biliary disease involves using an endoscope 310 to access a region in the gastrointestinal (GI) tract (FIG. 3) to which the gallbladder 14 is in close proximity 350, locating the gallbladder 14, accessing the gallbladder 14, and then treating the underlying condition that led to the need for intervention (FIG. 3). Treatments may also include, but are not limited to: providing for drainage of the gallbladder 14 and/or the biliary tree, delivering suitable substances or materials, such as antibiotics, inflammatory, and/or anti-inflammatory agents (any of which may be short-term acting, fast acting, or time release), and/or other substances (e.g. adhesives, bioadhesives, etc.) to the gallbladder 14 and/or biliary tree, removing gallstones 20, facilitating the destruction and subsequent removal of gallstones, clearing obstructions, delivering catheters, delivering stents (drug coated or not drug coated), temporarily or permanently defunctionalizing the cystic duct 16, temporarily or permanently defunctionalizing the gallbladder 14. Devices and therapies can be delivered in a single treatment, with minimal likelihood of or necessity for follow-up or repeat procedures.

Localization of the gallbladder 14 can be performed via endoscopic ultrasound (EUS) by accessing the wall of the GI tract with an endoscope 310 as shown in FIG. 3. Localization may also be achieved by any other method that visualizes anatomical features, such as fluoroscopy, x-rays, magnetic resonance imaging (MRI), computed axial tomography (CT) scans, ultrasound imaging from outside the body, or any method of anatomical imaging and visualization.

Once the gallbladder 14 has been located, it may be accessed and/or treated 350 through the wall of the GI tract (or any lumen in proximity to the gallbladder 14) with tools and devices (e.g. needles, guidewires, guidance catheters, dilators, shunts, etc.) delivered through or by, for example, an endoscope 310. Such tools and devices may be inserted down the length of the endoscope's working channel 312, or loaded onto or near the distal end of the endoscope 310. Alternately, tools and other devices may be used that do not require the aid of the endoscope for navigation or delivery. Direct visualization may be provided by the endoscope 310 during the procedure, as well as irrigation, suction, and insufflation.

Though the preferred location for accessing the gallbladder lumen is the duodenum 30, it may also be readily achieved through the wall of other regions of the GI tract, such as the stomach or the jejunum, for example. Thus, any lumen in close proximity to the gallbladder 14 is a candidate for access to and treatment of the gallbladder 14 and other members of the biliary system.

In order to defunctionalize the gallbladder 14, it may be beneficial to sclerose or necrotize the tissue inside the lumen of the gallbladder 14. This may involve only the tissue within the gallbladder 14, but it may also include, for example, the tissue comprising the cystic duct 16, which is the passageway leading into the gallbladder 14 from the common bile duct 18. Sclerosing or necrotizing the tissue within the gallbladder 14 may be achieved by using any ablating technique, such as cryoablation, thermal ablation, chemical ablation, radio frequency (RF) ablation, microwave ablation, and ultrasound ablation.

In the case of cryoablation, cold fluids (such as liquids, sprays, mists, and gases) may be applied to the walls of the lumen of the gallbladder 14 with an applicator 420 having a proximal end 402 and distal end 404 (FIG. 4). Any non-solid sclerosing agent may be similarly applied with an applicator. Such fluids may be applied evenly so that the effect is consistent throughout the affected areas, or they may be applied selectively or unevenly. The applicator 420 optionally includes a user controllable valve 440, as illustrated in FIG. 4E, within its lumen to facilitate control and application of the fluids or gases during the defunctionalization process. The user controllable valve can be positioned proximally from the delivery tip. The applicator 420 can be delivered through a working channel 412 of an endoscope 410.

Figure 4A:
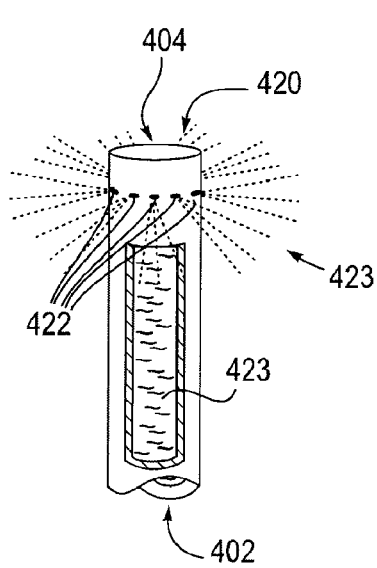
FIGS. 4A-E illustrate fluid applicator embodiments.
Figure 4B:
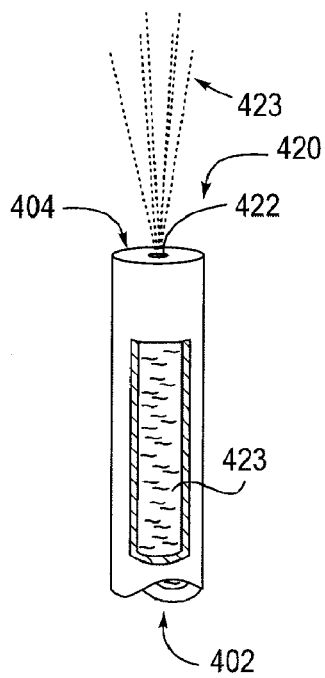
Figure 4C:
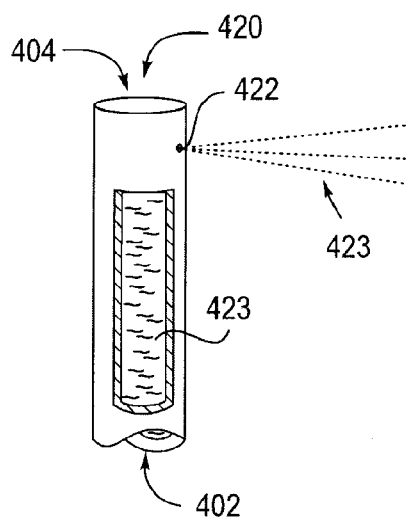
Figure 4D:
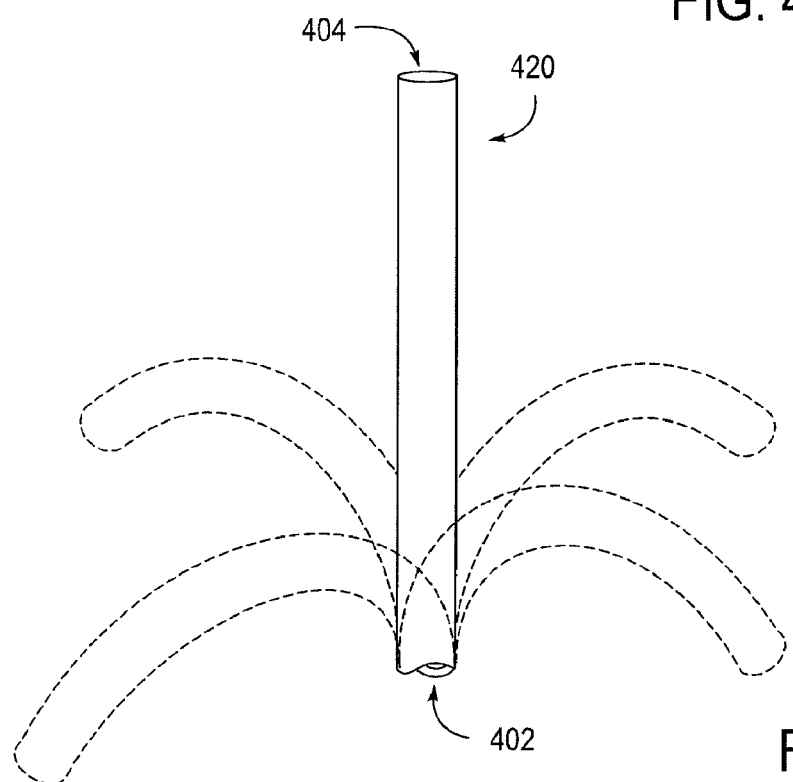
Figure 4E:
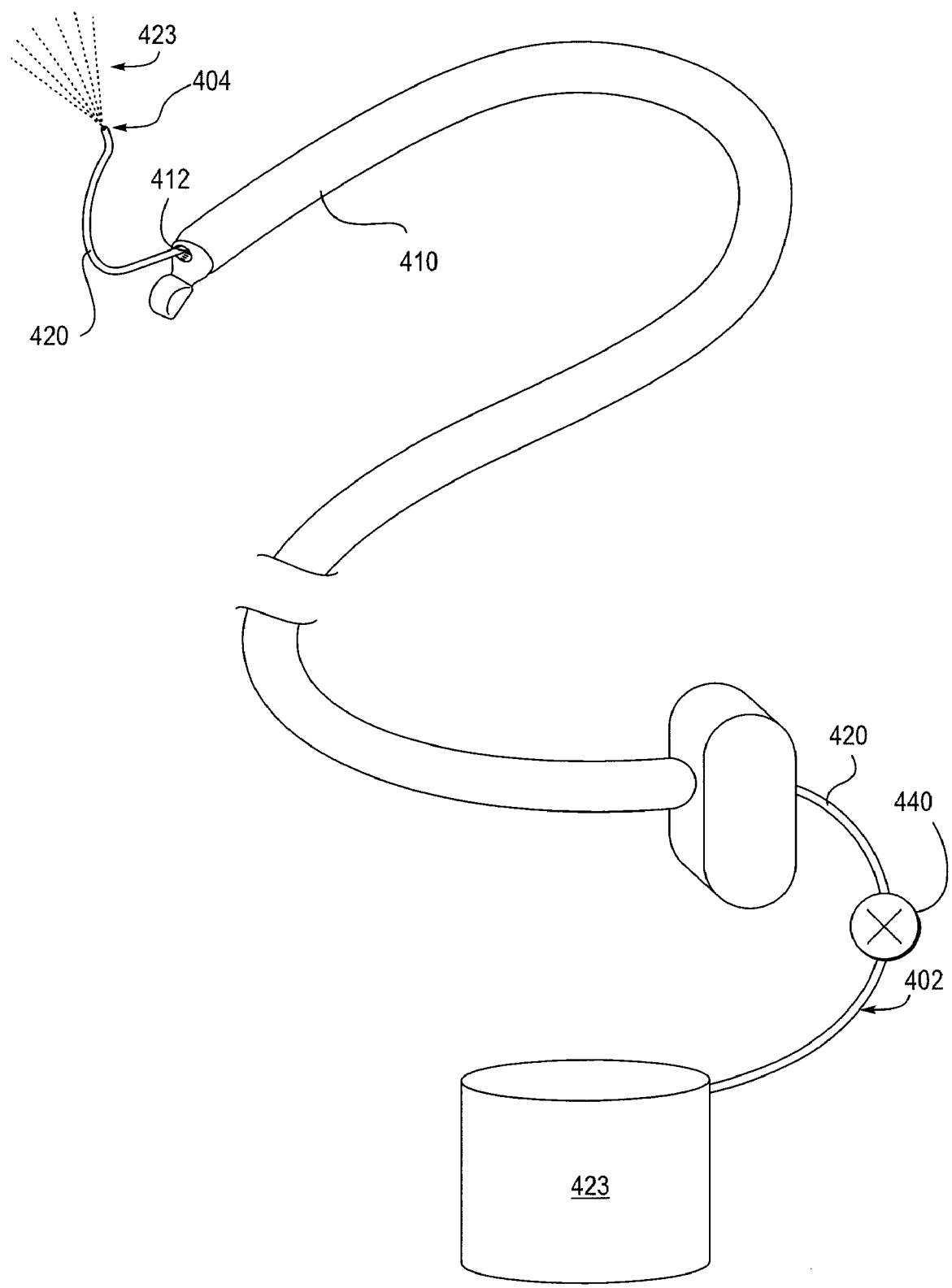
Figure 6:
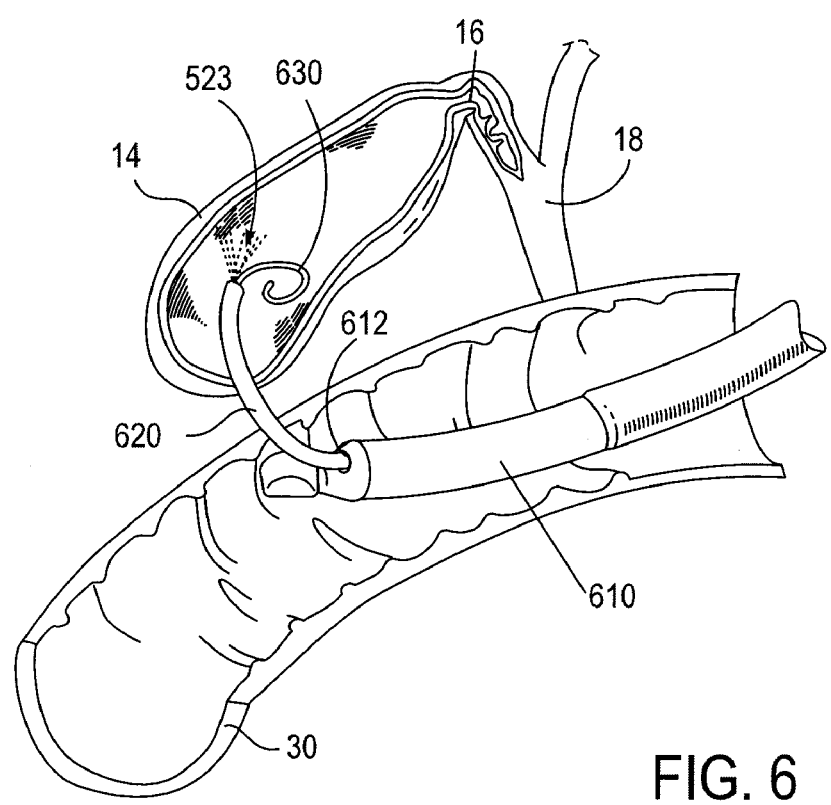
FIG. 6 illustrates a gallbladder defunctionalization device in combination with a guidance element.

During defunctionalization part or all of the walls may be treated. In order to have the ability to apply therapy anywhere within the gallbladder, it may be necessary to direct the application of such fluids by the applicator 420 at a variety of depths within the gallbladder 14, and at any or all angular orientations. The applicator 420 has one or more apertures 422 in communication with a central lumen through which fluid 423 or material is delivered. As discussed above, a controllable valve 440 is positioned within the interior lumen of the applicator 420 to provide control of the amount and timing of delivery. Different applicators 420 or nozzles may be useful for achieving this, such as those configurable to direct flow in a 360° radial pattern (FIG. 4A), a sharp stream or a cone shape directed forward by the applicator (FIG. 4B), or a sharp stream or a cone shape directed sideways by the applicator (FIG. 4C). The applicator 420 may be capable of articulating so that it may be selectively aimed (FIG. 4D). In order to distinguish treated areas from untreated areas, a pigment may be added to the fluid. Alternately, treated tissue may have a different appearance from untreated tissue due to the resulting sclerosis or necrosis. Applicators may be guided by one or more of a needle, a guidewire, and/or a guidance catheter, and controlled proximally by a clinician, as illustrated in FIG. 6. Alternately, applicators may navigate freely within the gallbladder. Applicators 620 may be delivered to the gallbladder lumen 14 through the tool channel 612 of an endoscope 610 and may remain within the endoscope during their use, or they may be guided into the gallbladder 14 using alternate guidance elements 630 (e.g. a needle, a guidewire, and/or a guidance catheter). In some instances, directly visualizing the devices and navigational devices used may also be desirable, and may facilitate control and treatment. Visualization may be achieved by any suitable mechanism known in the art, including, for example, endoscopic ultrasound (EUS), or by using a small daughter endoscope (e.g. a cystoscope), or by using catheters incorporating small imaging sensors at the distal end (e.g. Avantis' Third Eye) and fiber optic imaging bundles (e.g. Boston Scientific's SpyGlass). Visualization and guidance may also be achieved via external imaging methods, such as fluoroscopy (with or without the use of contrast agent), ultrasound, X-ray, etc. The outer diameter of the applicator 620 is smaller than a mammalian esophagus and can be larger than, for example, the diameter of the cystic duct 16 as illustrated.

Figure 5:
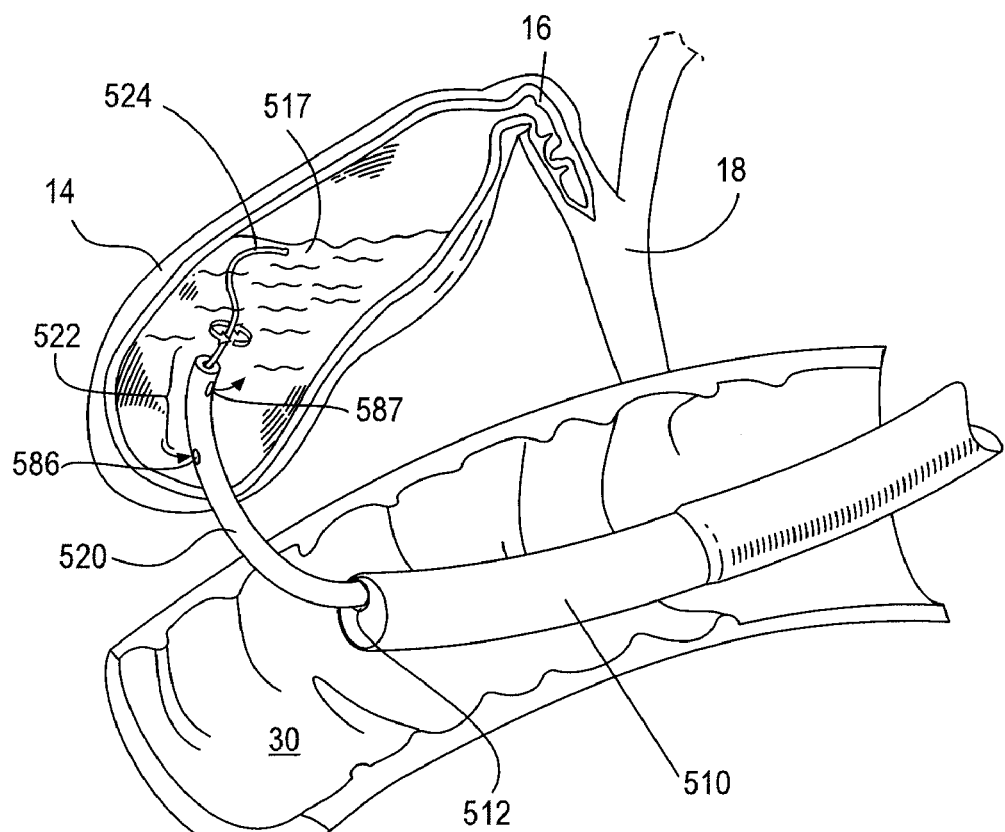
FIG. 5 illustrates a gallbladder defunctionalization method with a working fluid whose temperature is altered.

Additionally, cryoablation can be used to effect treatment by flooding the entire gallbladder lumen or duct lumen with a fluid 517 (FIG. 5). Localization of the gallbladder 14 can be performed via endoscopic ultrasound (EUS) by accessing the wall of the GI tract with an endoscope 510 as shown in FIG. 5. Thereafter, this can, for example, be performed with a liquid, but a gas may also be used. Filling the lumen, or substantially filling the lumen, with such a working fluid 517 ensures even distribution of treatment. The fluid or gas may be initially a first temperature and then be altered such that the temperature achieves a desired therapeutic level. An applicator for this approach may have one or more apertures 522 for introducing fluids 587 into the gallbladder and optionally withdrawing fluids 586 from the gallbladder. A stirrer 524 can be provided that stirs or mixes the fluid or gas 517 that is delivered into the lumen. This feature may ensure uniformity of properties throughout the working fluid or gas and increase the rate of temperature change (FIG. 5). The working fluid 517 may be left in place, or actively withdrawn after treatment is completed. As will be appreciated from FIG. 5, access to the gallbladder 14 can be achieved through the wall of the duodenum 30. The outer diameter of the applicator 520 is smaller than a mammalian esophagus and larger than, for example, the diameter of the cystic duct 16 as illustrated.

In cases when the activatable material, such as a working fluid or gas 517, remains in the gallbladder lumen or duct lumen, it may be selected so that it becomes a biocompatible gel or foam once it has reached a specific state, such as a low or high temperature, or contact with an activating agent, or when sufficient time has passed. The activating agent may be selected to be bile, so that the gel or foam becomes further activated in the presence of flow of bile. In this way, it a self-sealing mechanism is established. Such a foam or gel may also be selected so that it is bioabsorable, and is self dissipating after a desired period of time.

An amount of fluid, gas, or material delivered as described throughout can be such that it fills the gallbladder, substantially fills the gallbladder (e.g., fills more than 50% of the gallbladder, more than 75% of the gallbladder, more than 85% of the gallbladder, more than 90% of the gallbladder, more than 95% of the gallbladder, or more than 99% of the gallbladder) or is activatable to fill or substantially fill the gallbladder. Alternatively, in some instances, e.g., where a vacuum is applied, the amount of fluid, gas, or material delivered as described throughout can be such that it coats the interior lumen of the gallbladder, or substantially coats the interior lumen of the gallbladder (e.g., coats more than 50% of the gallbladder, more than 75% of the gallbladder, more than 85% of the gallbladder, more than 90% of the gallbladder, more than 95% of the gallbladder, or more than 99% of the gallbladder).

In contrast to cryoablation, thermal (or heat) ablation may be applied to effect treatment. The same methods outlined above for cryoablation may also be used in the application of therapies based on heat ablation. This includes using working fluids that may be applied using a spray applicator, working fluids that completely fill, or substantially fill, the lumen, working fluids that are introduced at a non-therapeutic temperature and then altered so that the temperature is increased to therapeutic levels, and fluids that become gels or foams at a desired elevated temperature. These techniques may be used with any fluid or non-solid sclerosing agents in addition to those described above. In another approach thermal ablation is achieved through the use of infrared light to heat the tissue comprising the gallbladder 14 and/or cystic duct 16.

Another alternate method of defunctionalizing the gallbladder 14 involves applying a vacuum. After occlusion of, for example, the cystic duct 16, application of a vacuum to the gallbladder lumen causes it to collapse to a smaller volume. The internal volume of the gallbladder lumen may be eliminated altogether. Making this collapsed volume permanent or semi-permanent results in the goal of defunctionalizing the gallbladder 14. Substances may be applied to the gallbladder walls prior to the application of vacuum, such as a bioadhesives, sclerosing agents, or fluids used in cryo- or thermal ablation. These fluids may serve to enhance the outcome or improve the efficacy of the treatment.

The devices and methods disclosed herein facilitate defunctionalizing the gallbladder without the need for surgery.

Kits:

All of the devices required to deliver and install a conduit, treat and/or defunctionalize the gallbladder, may be packaged in a kit. Bundling all devices, tools, components, materials, and accessories needed to perform these procedures into a kit may enhance the usability and convenience of the devices, and also improve the safety of the procedure by encouraging clinicians to use the items believed to result in the best outcomes. The kit may be single-use or reusable, or it may incorporate some disposable single-use elements and some reusable elements. The kit may contain, but is not limited to, the following: implantable and/or non-implantable devices; delivery devices (e.g. needles, guidewires, guidance catheters, dilators, etc.); balloon inflation/deflation accessories; syringes; fluid flow, temperature, and pressure measurement instruments; scissors; scalpels; clips; ablation catheters; endoscopic tools (e.g. lithotripsy devices, snares, graspers, clamps, forceps, etc.); fluids; gels; gas cartridges adaptable to communicate with the devices. The kit may be supplied in a tray, which organizes and retains all items so that they can be quickly identified and used.

Description of Other Uses

The techniques and devices described in this application may prove beneficial in applications beyond their initial use in the treatment of biliary disease.

Figure 1:
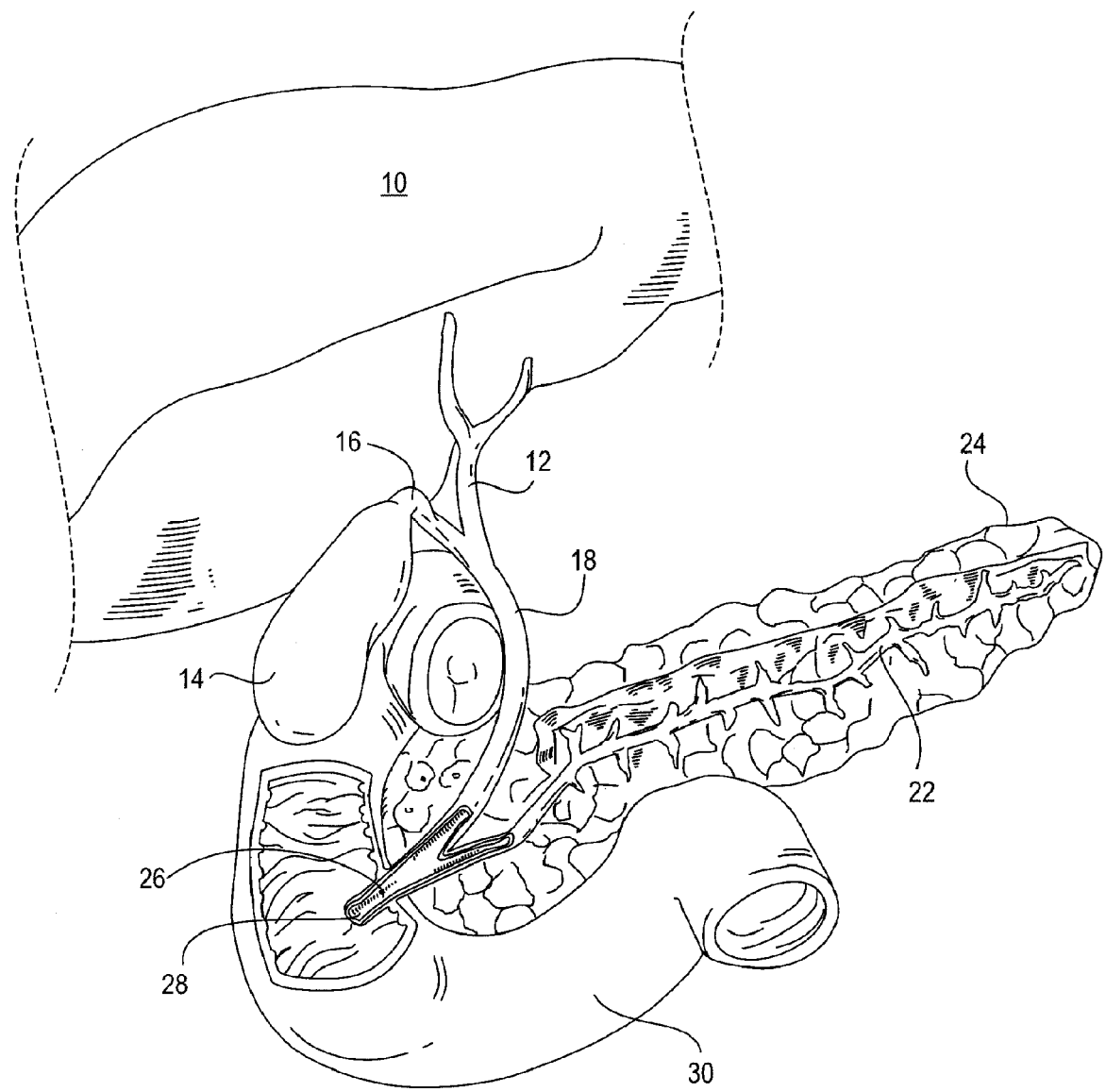
FIG. 1 illustrates an overview of the biliary system.
Figure 2:
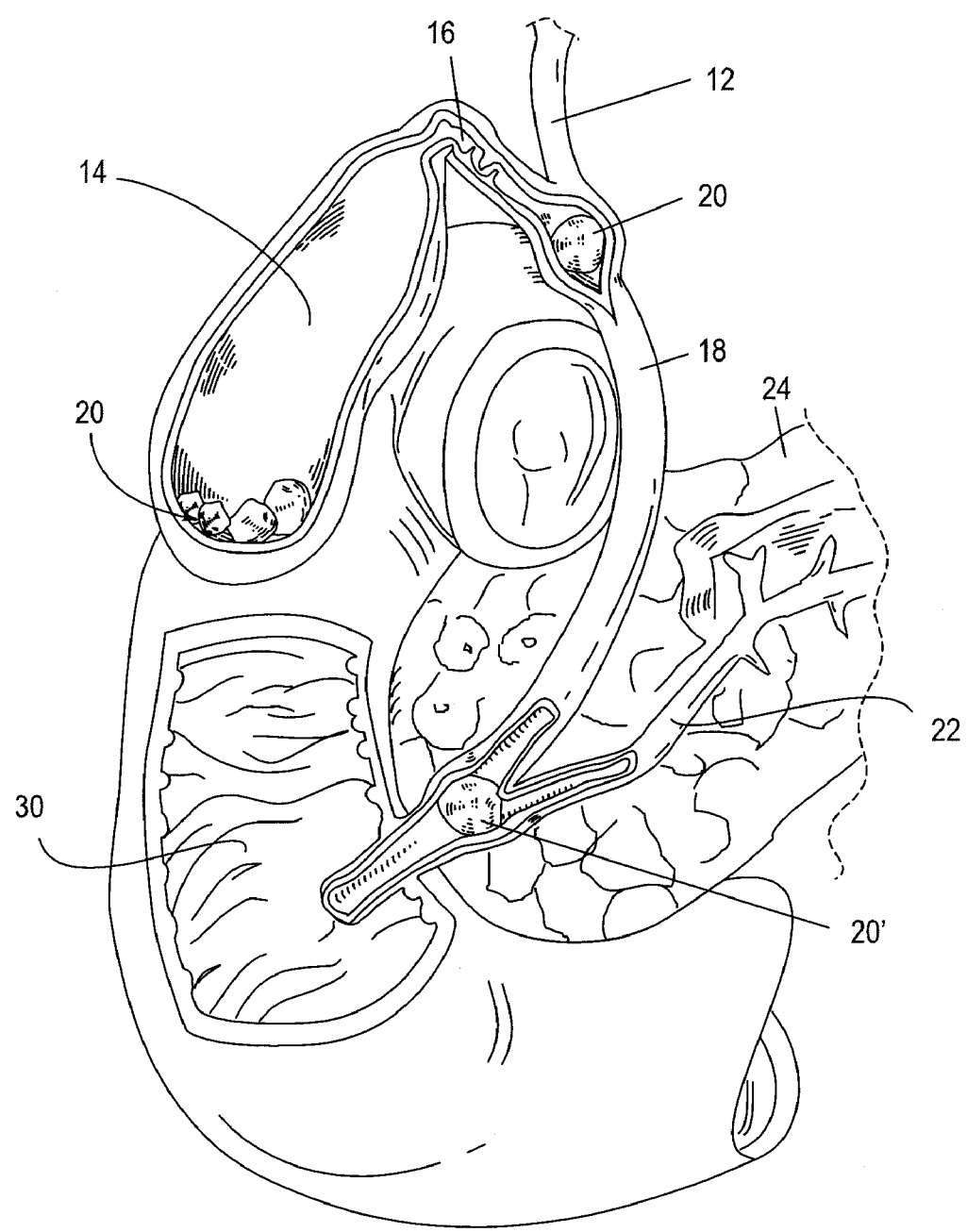
FIG. 2 illustrates the biliary system with gallstones.

For example, they may prove to be an effective mechanism of treating cholangitis (infection of the common bile duct 18). This condition is usually bacterial, and occurs when the bile duct is blocked by gallstones 20' or a tumor. Traditional treatment involves the insertion a stent or drainage catheter into the common bile duct 18 to allow bile to drain into the duodenum from locations above the obstruction. Placement of a conduit into the gallbladder 14 may allow for an alternate method of draining bile and/or other fluids into the duodenum. Any blockage in the common bile duct 18 between the entrance of the cystic duct and the duodenum may be treated in this way. See FIG. 2.

Another use of the devices and techniques described herein is for drainage of any body lumen into another body lumen in proximity, for example, the drainage of pancreatic pseudocysts.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. An applicator for endoscopic delivery to treat biliary disease, comprising:
   an elongated member having a proximal end and a distal end adapted to be delivered transluminally from an exterior surface of a gallbladder to an interior lumen of the gallbladder without use of a common bile duct, the elongated member having a length adapted for delivery through a mammalian esophagus, stomach and duodenum, and an outer diameter smaller than a mammalian esophagus;
   a lumen positioned within the elongated member with an aperture at the distal end of the elongated member, wherein the lumen within the elongated member extends a length of the elongated member and is sized to deliver at least one of a guiding element or a stirring element through the aperture at the distal end of the elongated member;
   one or more material delivery apertures positioned at the distal end of the elongated member and sharing a coplanar relationship to another of the one or more material delivery apertures, wherein the one or more material delivery apertures configured to deliver a material to the interior lumen of the gallbladder or a gallbladder duct, wherein the one or more delivery apertures are configured to deliver the material in a 360 degree radial pattern, wherein the one or more material delivery apertures are in fluid communication with the lumen within the elongated member, and wherein the one or more material delivery apertures have a smaller diameter than the aperture of the lumen within the elongated member; and
   a valve positioned within the lumen within the elongated member, wherein the valve is configured to control an amount and a timing of the delivery of the material to the interior lumen of the gallbladder.

2. The applicator of claim 1, wherein the distal end has an angular orientation relative to the length of the elongated member.

3. The applicator of claim 1, wherein the distal end is configured to deliver the material with at least one of a sharp stream and a cone shape.

4. The applicator of claim 1, wherein the distal end has an articulating member.

5. The applicator of claim 1, further comprising a vacuum element configured to apply a vacuum to the gallbladder or the gallbladder duct.

6. The applicator of claim 1, wherein the distal end is configured to apply an adhesive to the interior lumen of the gallbladder.

7. The applicator of claim 1, wherein the applicator is configured for deployment by an endoscope.

8. The applicator of claim 1, wherein the applicator is configured for deployment using at least one of a needle, a guidewire, or a guidance catheter.

9. The applicator of claim 1, wherein the lumen within the elongated member is configurable to provide restrictable fluid flow.

10. The applicator of claim 1, further comprising one or more fluid control components.

11. The applicator of claim 1, wherein the valve comprises a user-controllable flow-restrictor valve.

12. The applicator of claim 1, wherein the valve comprises a one-way valve configured to only allow the material to flow therethrough toward the one or more material delivery apertures.

13. The applicator of claim 1, wherein the elongated member is flexible and wherein the elongated member is an elongate tube configured to extend into the gastrointestinal tract.

14. A kit for treating biliary disease comprising:
   a device comprising:
   an elongated member having a proximal end and a distal end adapted to be delivered transluminally from an exterior surface of a gallbladder to an interior lumen of the gallbladder;
   a lumen positioned within the elongated member with an aperture at the distal end of the elongated member, wherein the lumen within the elongated member extends a length of the elongated member and is sized to deliver at least one of a guiding element or a stirring element through the aperture at the distal end of the elongated member;
   one or more material delivery apertures positioned at the distal end of the elongated member and sharing a coplanar relationship to another of the one or more material delivery apertures, wherein the one or more material delivery apertures configured to deliver a material to the interior lumen of the gallbladder or a gallbladder duct, wherein the one or more delivery apertures are configured to deliver the material in a 360 degree radial pattern, wherein the one or more material delivery apertures are in fluid communication with the lumen within the elongated member, and wherein the one or more material delivery apertures have a smaller diameter than the aperture of the lumen within the elongated member;
   a valve positioned within the lumen within the elongated member, wherein the valve is configured to control an amount and a timing of the delivery of the material to the interior lumen of the gallbladder;

an ablation device configured to ablate tissue of the gallbladder; and the material to be delivered to the gallbladder or the gallbladder duct.

15. The kit of claim 14, wherein the material comprises a sclerosing agent, an antibiotic, an inflammatory agent, an anti-inflammatory agent, a biocompatible gel, or a biocompatible foam.

16. The kit of claim 14, further comprising a needle, a guidewire, or a guidance catheter configured to deploy the device.

17. The kit of claim 14, further comprising a temperature measurement instrument.

18. The kit of claim 14, further comprising a pressure measurement instrument.

19. An applicator for endoscopic delivery to treat biliary disease, comprising:

an elongated member having a proximal end and a distal end adapted to be delivered transluminally from an exterior surface of a gallbladder to an interior lumen of the gallbladder without use of a common bile duct, the elongated member having a length adapted for delivery through a mammalian esophagus, stomach and duodenum, and an outer diameter smaller than a mammalian esophagus;

a lumen positioned within the elongated member with an aperture at the distal end of the elongated member, wherein the lumen within the elongated member extends a length of the elongated member and is sized to deliver at least one of a guiding element or a stirring element through the aperture at the distal end of the elongated member;

a nozzle coupled to the distal end of the elongated member, the nozzle comprising one or more material delivery apertures and configured to deliver a material to the interior lumen of the gallbladder or a gallbladder duct, wherein the one or more delivery apertures is configured to deliver the material in a 360 degree radial pattern, wherein the nozzle and the one or more material delivery apertures are in fluid communication with the lumen within the elongated member, and wherein the one or more material delivery apertures have a smaller diameter than the aperture of the lumen within the elongated member; and a valve positioned within the lumen within the elongated member, wherein the valve is configured to control an amount and a timing of the delivery of the material to the interior lumen of the gallbladder.

* * * * *